United States Patent [19]

Jelly

[11] Plant 4,057

[45] May 31, 1977

[54] ROSE PLANT NAMED ROYALTY

[75] Inventor: Robert G. Jelly, Richmond, Ind.

[73] Assignee: E. G. Hill Co., Inc., Richmond, Ind.

[21] Appl. No.: 683,905

[22] Filed: May 6, 1976

[51] Int. Cl.[2] ..... A01H 5/00

[52] U.S. Cl. ..... Plt./29

[58] Field of Search ..... Plt./20–21, Plt./28–29

*Primary Examiner*—Robert E. Bagwill

*Attorney, Agent, or Firm*—Chas. W. Rummler

[57] ABSTRACT

A new rose plant cultivar intended for greenhouse culture for the production of cut flowers, distinguished by its uniform growth and cane quality with less blind wood, the exceptional vase life of its relatively slow opening flowers, when ready to cut, which makes them easier to handle in periods of high production, the exceptional timing characteristic and opening flower form of its deep red flowers, and the good response of this plant to lower temperature rose growing conditions.

1 Drawing Figure

BACKGROUND OF THE NEW PLANT

This new rose plant originated as a seedling resulting from my cross of "Forever Yours" (U.S. Plant Pat. No. 2,443) with "Love Affair" (U.S. Plant Pat. No. 3,287) at Richmond, Ind., in the spring of 1970 with the object of developing a rose that would combine the good qualities of both parents and also have good response to the lower temperature growing conditions necessitated by current energy problems.

My new plant produced its first flower in the spring of 1971 and because of the beautiful solid red coloring of its blooms, this plant was selected for reproduction and test. Asexual propagation of this new plant by budding was carried on at Richmond, Ind., under my direction and several years of observation of the progeny of this plant and succeeding propagations by grafting at Pleasanton, Calif., have demonstrated that this new rose variety has fulfilled my objectives and that its distinctive characteristics are firmly fixed and hold true from generation to generation.

DESCRIPTION OF THE DRAWING

This new variety of rose plant is illustrated by the accompanying full color photographic drawing which shows the form of the fully opened flower and three stages of the buds, typical leaves of this variety, a specimen of young wood with leaves and a specimen of old stem, and a side view showing the reproductive organs of a flower after the petals have been removed, the colors shown being as nearly true as can be reasonably done by conventional photographic procedures.

DESCRIPTION OF THE NEW PLANT

The following is a detailed description of my new rose plant with color designations according to the Horticultural Colour Chart (HCC) produced by Robert S. Wilson in collaboration with the British Colour Council and published by The Royal Horticultural Society at London, England, or according to the Horticultural Colour Chart (RHS) of the Royal Horticultural Society, the following data being from observations of greenhouse plants grown at Richmond, Ind.

THE PLANT

Origin: Seedling.

Parentage: Seed parent — Forever Yours (P.P. 2,443). Pollen parent — Love Affair (P.P. 3,287).

Classification: Grandiflora, but disbudded commercially to a Hybrid Tea form.

Form: Bush.

Habit: Upright and much branched.

Growth: Vigorous and moderately free.

*Canes.*—Medium in diameter.

*Main stems.*—Color — Spinach Green 0960/1 (HCC). Thorns: Few; medium in length, downwardly hooked from a long narrow base. Color: Greyed Orange 165A (RHS). Prickles: Very few. Color: Greyed Orange 167B (RHS) at base to translucence at the tip. Hairs: None.

*Branches.*—Color — Spinach Green 0960/1 (HCC). Thorns: Few, of medium length, hooked downwardly from a long base. Color: Greyed Red 182C (RHS) at the base to a translucent tip. Prickles and hairs: None.

Foliage: Quantity — Average.

*Leaves.*—Size — Medium to large. Shape: Odd pinnate 3 to 7 leaflets. Leaflets: Shape — Oval with cuspidate apex and obtuse base and with an irregularly serrate margin. Color — Mature Upper Surface — Green 139A (RHS); Under Surface — A shade lighter than Greyed Green 191A (RHS). Young Upper Surface — A shade between Spinach Green 0960 (HCC) and Parsley Green 00962/3 (HCC) with mid vein and the margin a shade between Greyed Red 178B (RHS) and Greyed Red 178C (RHS). Under Surface — Lavender Green 000761 (HCC) with veination and margin Greyed Red 182A (RHS).

*Rachis.*—Heavy. Upper Side: Grooved and prickly. Under Side: Thorny.

*Stipules.*—Long and narrow, with short to medium long points which turn out at an angle of more than 45°, some recurving toward the stem.

THE BUD

Before calyx breaks:

*Size.*—Medium large.

*Form.*—Short pointed and globular, with conspicuous neck and with foliaceous appendages on the surface of the bud, and with slender slightly bristle-like foliaceous parts extending beyond the tip of the bud equal to ½ to ¾ of the length.

*Color of calyx.*—Yellow Green 144B (RHS) at the base shading to a color between Green 143A (RHS) and Green 141C (RHS) with foliaceous parts Spinach Green 0960/1 (HCC).

As calyx breaks:

*Outside color.*—Greyed Purple 185A (RHS).

As First Petal Opens:

*Bud size.*—Medium large. Form: Long pointed.

*Color of petal.*—Outside — Chrysanthemum Crimson 824 (HCC) highlighted with Red 53A (RHS). Inside — More velvety than Red 53A.

Bud opening: Bud opens up well.

*Effect of hot dry weather.*—A slight decrease in size and slightly lighter color intensity.

Sepals: Permanent and of short to medium length.

*Shape.*—Long pointed. Sepals are generally flat and fall back toward the stem as bud opens.

*Color.*—Inside — Spinach Green 0960 (HCC) at the tip through Spinach Green 0960/2 (HCC) to a shiny shade of Yellow Green 145B (RHS) at the base and streaked toward the center. Outside — A shade slightly darker than Green 143A (RHS) with Yellow Green 145B (RHS) at the base.

*Peduncle:* Strong and erect, with long length and large diameter.

*Bark.*—Smooth. Color: Yellow Green 144B (RHS) faintly mottled with Green 143C (RHS).

*Thorns.*—None.

*Prickles.*—Numerous. Color: Greyed Red 182A (RHS) with a translucent tip.

*Hairs.*—None.

THE FLOWER

Blooming habit: Continuous and free blooming.

Size: 4 to 4½ inches in diameter when fully opened.

Borne: Several to a stem in regular pyramidal clusters on long, strong stems. Stem is disbudded to one flower for commercial use.

Shape: High centered at first with petals loosely rolled outward, becoming cupped at maturity with petals slightly rolled outward.

Petalage: Double — 20 to 22 petals arranged regularly.

*Shape of Petals.*—Outside — Oval, most with cuspidate apex, some with mucronate apex and 1 or 2 notches. Intermediate — Oval, mucronate apex and 1 or 2 notches. Inside — Oval, apex mucronate with 1 or 2 notches.

*Aspect.*—Inside — Velvety; Outside — Satiny.

*Texture.*—Leathery and moderately thick.

*Color.*—Petal colors may be modified by being bordered, penciled or shaded with other colors.

A. The following observations are of a newly opened greenhouse flower in November, 1975.

Outside petals:

*Outside surface.*—Greyed Yellow 160B (RHS) at the base, shaded to slightly darker than Cardinal Red 822/2 (HCC) in petal body.

*Inside surface.*—yellow 160C (RHS) at the base, shaded through China Rose 024 (HCC) to a main color of a shade between Currant Red 821/2 (HCC) and Red 53B (RHS) but more brilliant than both.

Intermediate petals:

*Outside surface.*—Greyed yellow 160D (RHS) at the base through China Rose 024/1 (HCC) to a main color Cardinal Red 822/1 (HCC).

*Inside surface.*—Greyed Yellow 160C (RHS) at the base through Rose Red 724/3 (HCC) to a main color of Cardinal Red 822/1 (HCC).

Inner petals:

*Outside surface.*—A shade slightly lighter than Greyed Yellow 160B (RHS) shaded through China Rose 024/1 (HCC) to a main color slightly darker than Red 53C (RHS).

*Inside surface.*—Greyed Orange 163D (RHS) at the base, shaded through Rose Red 724/1 (HCC) to a main color of a shade between Red 53A (RHS) and Cardinal Red 822/2 (HCC).

B. The following observations are of a rose opened for three days in greenhouse in November, 1975.

Outside petals:

*Outside surface.*—Greyed Yellow 160C (RHS) at the base through Rose Red 724/3 (HCC) to a main color shade slightly darker than Rose Red 724 (HCC).

*Inside surface.*—Greyed Yellow 160B (RHS) at the base through Red Purple 57C (RHS) to a main color shade between Currant Red 821 (HCC) and Rose Red 724 (HCC) but darker and more velvety than either.

Intermediate petals:

*Outside surface.*—Greyed Yellow 160D (RHS) at the base through shades of Rose Madder 23/1 (HCC) to a main color of Rose Red 724 (HCC).

*Inside surface.*—Green Yellow 1D (RHS) at the base through Rose Red 724/2 (HCC) to a shade between Rose Red 724 (HCC) and Cardinal Red 822/3 (HCC) but more brilliant than both.

Inner petals:

*Outside surface.*—Yellow 6D (RHS) at the base through Red Purple 57D (RHS) to a main color shade slightly darker than China Rose 024 (HCC).

*Inside surface.*—Yellow 10D (RHS) at the base shaded through China Rose 024/1 (HCC) to a main color shade more brilliant than Currant Red 824/3 (HCC) and slightly darker than Rose Red 724 (HCC).

General color effect:

*Newly opened flower.*—A shade more brilliant than Cardinal Red 822/3 (HCC).

*Three days opened flower.*—A shade slightly darker, but more brilliant and velvety than Rose Red 724 (HCC).

Persistence: Petals hang on.

Effect of weather: In hot, dry weather, the colors fade to Rose Red 724 (HCC).

Fragrance: Moderate centifolia.

Lasting quality: 8 to 10 days at living room temperatures in November.

REPRODUCTIVE ORGANS

Stamens: Number — Medium, arranged regularly and mixed with petaloids.

*Filaments.*—Medium in length, most with anthers. Color: Greyed yellow 160C (RHS) at base to Greyed Purple 184D (RHS) for the main color.

*Anthers.*—Large; all open at once. Color: Greyed Yellow 160C (RHS) with a margin of Greyed Yellow 162B (RHS).

*Pollen.*—Sparse. Color: Greyed Yellow 162B (RHS).

Pistils: Many in number.

*Styles.*—Uneven, long, very thin and bunched. Color: White 155C (RHS) at the base to Red 52A (RHS) just below stigma.

*Stigmas.*—Color — Orange White 159B (RHS).

Ovaries: Some protruding from calyx.

Hips: Medium in length. Gourd shaped with globular body and conspicuous neck, with very smooth and thin walls.

Seeds: Many of medium size.

My new variety of rose plant is an improvement over its seed parent "Forever Yours" in that it has less blind wood, improved opening flower form and better vase life. The flowers of the new plant are also slower opening, when ready to cut, and are thus easier to handle than those of its parent during periods of high production.

This new variety is better than its pollen parent "Love Affair" in at least two major respects. It is uniform in growth and cane quality and it does not have the lack of uniformity of timing often exhibited by its pollen parent.

The uniform growing characteristic of this new rose together with its exceptional timing and vase life enhance its commercial value as a producer of cut flowers of superior character.

I claim:

1. A new and distinct cultivar of rose plants "Forever Yours" × "Love Affair" substantially as herein shown and described, characterized by its uniform growth and cane quality with less occurrence of blind wood, its uniform timing and improved vase life, and the slower opening of its buds when ready to cut and its improved opening flower form.

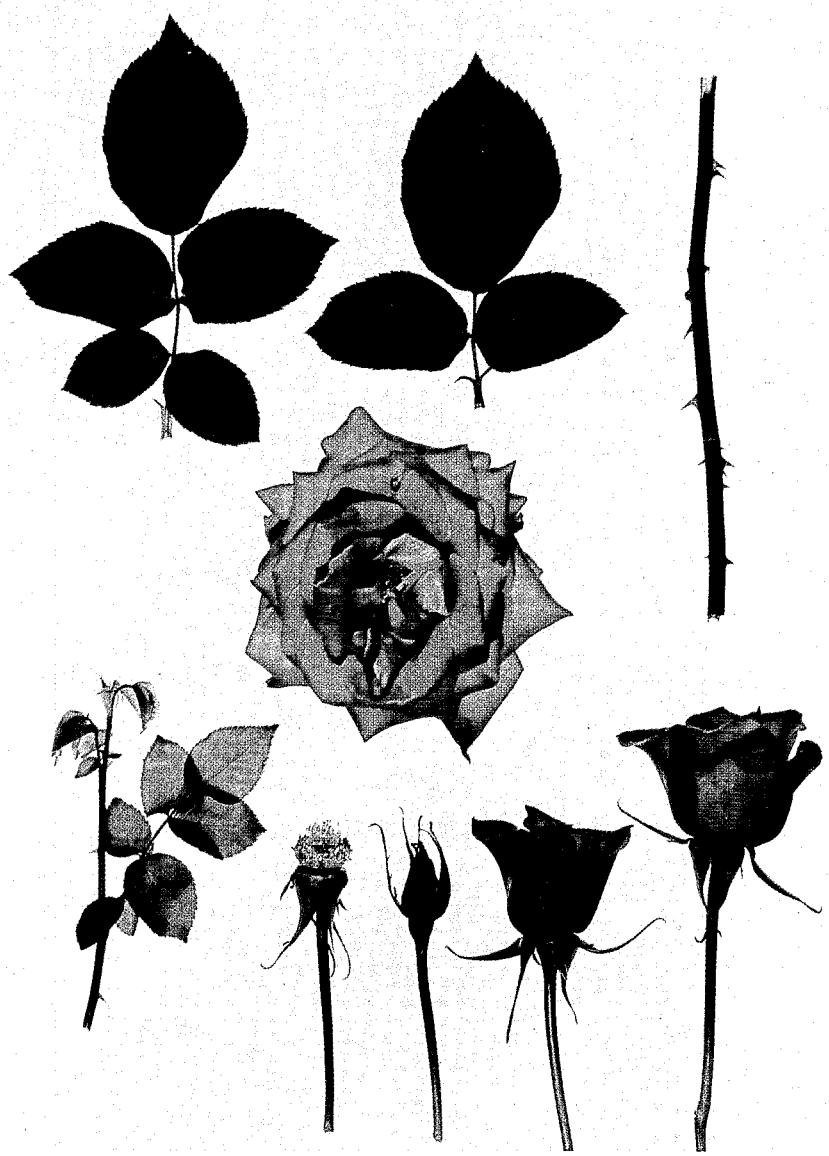

* * * * *